United States Patent
Buchtal et al.

(10) Patent No.: US 11,555,780 B2
(45) Date of Patent: Jan. 17, 2023

(54) PHOTOACOUSTIC SENSOR WITH REPLACEMENT GAS AND DETECTION PROCESS USING SUCH A SENSOR

(71) Applicant: Drägerwerk AG & Co. KGaA, Lübeck (DE)

(72) Inventors: Ralf Buchtal, Lübeck (DE); Gerd Peter, Lübeck (DE); Bernd-Michael Dicks, Lübeck (DE); Björn Spilker, Lübeck (DE); Robert Jahns, Lübeck (DE); Martin Kroh, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 13 days.

(21) Appl. No.: 17/380,529

(22) Filed: Jul. 20, 2021

(65) Prior Publication Data
US 2022/0026346 A1 Jan. 27, 2022

(30) Foreign Application Priority Data
Jul. 21, 2020 (DE) ...................... 10 2020 119 094.8

(51) Int. Cl.
*G01N 21/17* (2006.01)
*G01N 33/00* (2006.01)

(52) U.S. Cl.
CPC ..... *G01N 21/1702* (2013.01); *G01N 33/0036* (2013.01); *G01N 2021/1704* (2013.01)

(58) Field of Classification Search
CPC .......... G01N 21/1702; G01N 21/1704; G01N 33/0036; G01N 2021/1704;
(Continued)

(56) References Cited

U.S. PATENT DOCUMENTS 5,923,035 A 7/1999 Winkler et al.
8,085,403 B2* 12/2011 Fritz ................... G01N 21/1702
356/437
(Continued)

FOREIGN PATENT DOCUMENTS

DE 102012217479 B3 10/2013
DE 102016216875 A1 3/2017

OTHER PUBLICATIONS

Fraunhofer-Institut Für Physikalische Messtechnik Ipm: Miniaturisierte photoakustische Gasmesssysteme. May 2017.
(Continued)

*Primary Examiner* — Suman K Nath
(74) *Attorney, Agent, or Firm* — McGlew and Tuttle, P.C.

(57) ABSTRACT

A photoacoustic sensor (100) is capable of detecting a predefined target gas in an area (Um). A process is capable of detecting the target gas with the use of such a sensor (100). A sample chamber (3) holds a gas sample (Gp) to be tested. Electromagnetic waves (eW) from a radiation source (1) pass through the sample chamber (3) and the detection chamber (4). The waves elicit in the detection chamber (4) an acoustic effect, which is measured by an acoustic sensor (7). The acoustic effect is correlated with the concentration of the target gas in the sample chamber (3). The detection chamber (4) is fluid-tightly sealed, is free from target gas and is filled with a replacement gas (Eg). The transmission of the replacement gas (Eg) has a spectral response similar to that of the transmission of the target gas in a predefined target gas wavelength range.

19 Claims, 4 Drawing Sheets

(58) Field of Classification Search
CPC ........... G01N 29/2425; G01N 29/2418; G01N 29/2431; G01N 29/326
See application file for complete search history.

(56) References Cited

U.S. PATENT DOCUMENTS

| | | |
|---|---|---|
| 10,527,589 B2 | 1/2020 | Kolb et al. |
| 10,753,858 B2 * | 8/2020 | Kolb ................... G01N 29/022 |
| 11,137,376 B2 * | 10/2021 | Eberl ................ G01N 29/2425 |
| 11,143,627 B2 * | 10/2021 | Chafekar ............ G02F 1/13439 |
| 11,231,394 B2 * | 1/2022 | Reingruber .......... G01N 29/036 |
| 11,353,431 B2 * | 6/2022 | Bretthauer ............. G01N 15/06 |
| 2009/0071226 A1 | 3/2009 | Studer et al. |
| 2015/0020569 A1 | 1/2015 | Ostermann et al. |
| 2016/0103092 A1 | 4/2016 | Nauber et al. |
| 2016/0178412 A1 | 6/2016 | Dittrich et al. |

OTHER PUBLICATIONS

Gehring, H.: Monitoring der Beatmung während der Anästhesie. vol. 27: Refresher Course, Aktuelles Wissen für Anästhesisten. Deutsche Akademie für Anästhesiologische Fortbildung, 2001, S. 81-105.

El-Safoury, M. [et al.]: Miniaturized photoacoustic detection of organofluorine-based refrigerants. Journal of Sensors and Sensor Systems, vol. 9, May 3, 2020, S. 89-97.

\* cited by examiner

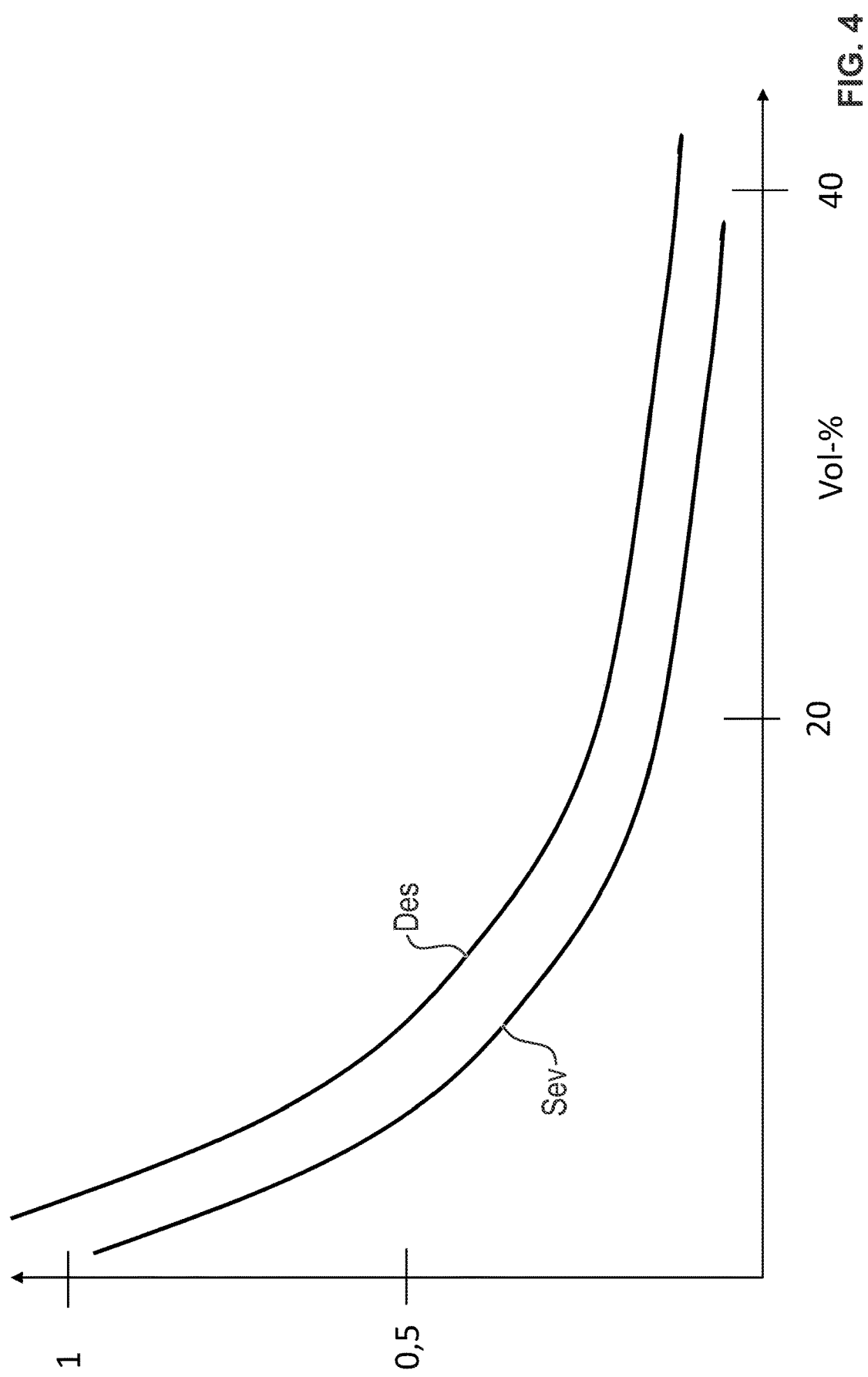

PHOTOACOUSTIC SENSOR WITH REPLACEMENT GAS AND DETECTION PROCESS USING SUCH A SENSOR

CROSS REFERENCE TO RELATED APPLICATIONS

This application claims the benefit of priority under 35 U.S.C. § 119 of German Application 10 2020 119 094.8, filed Jul. 21, 2020, the entire contents of which are incorporated herein by reference.

TECHNICAL FIELD

The present invention pertains to a photoacoustic sensor, which is capable of detecting at least one target gas in an area to be monitored. The target gas or at least one target gas is especially an anesthetic or a solvent. Furthermore, the present invention pertains to a process for detecting the target gas or at least one target gas with the use of such a photoacoustic sensor.

TECHNICAL BACKGROUND

Various photoacoustic sensors have become known.

DE 10 2012 217 479 B3 describes a gas sensor 1, which is capable of determining the concentration of a target gas in a gas mixture, namely, the concentration of a hydrocarbon, especially methane, in the exemplary embodiment described there. A test gas volume 11 is capable of accommodating a gas sample containing the target gas. A fluid-tight reference gas volume 12 with a housing 120 holds a mixture of the target gas and a buffer gas. The buffer gas improves the speed of response or the sensitivity or the accuracy of the gas sensor 1. For example, the buffer gas has a gas mixture between 1% and 20% and is, for example, sulfur hexafluoride ($SF_6$). A radiation source 3 emits narrow-band or broad-band electromagnetic radiation 30. The radiation 30 passes through the test gas volume 11 and the reference gas volume 12. The radiation 30 elicits in the reference gas volume 12 an acoustic effect, and a resonance body 2 consisting of a piezoelectric material or a microresonator 20 is capable of measuring the acoustic effect.

A photoacoustic sensor, which measures the concentration of carbon dioxide ($CO_2$) in the ambient air, is described in a document of the Fraunhofer-Institut für Physikalische Messtechnik (IPM) entitled "Miniaturized Photoacoustic Gas Measuring Systems," available under https://www.ipm.fraunhofer.de/content/dam/ipm/de/PDFs/produktblaetter/GP/ISS/photokustisehe-gas-messysteme-miniaturisiert.pdf, downloaded on May 18, 2020. A thermal emitter emits modulated electromagnetic waves in the infrared range into a measuring path. The IR waves pass through the measured path and impact a detection chamber, which is likewise filled with carbon dioxide and optionally with an admixture of noble gases. A microphone at the detection chamber detects an acoustic effect in the form of pressure fluctuations, which are generated by the modulated waves. The gas in the detection chamber absorbs a part of the IR waves. The absorption in the measured path is more intense and a signal generated by the microphone is consequently weaker when the ambient air in the measured path has a higher concentration of $CO_2$.

Requirements imposed on an anesthesia workplace are listed with reference to EN740 in H. Gehring: "Monitoring of Ventilation During Anesthesia," Volume 27: Refresher Course, Current Knowledge for Anesthesiologists, Deutsche Akademie für Anästhesiologische Fortbildung, 2001, pp. 81-105. The anesthetic gas concentration is to be measured in the gas fed by inhalation, in the patient port or in the Y-piece at the tube. For example, photoacoustic spectroscopy is used for this purpose. Infrared light of a defined wavelength is sent in a pulsed form through the measuring chamber, as a result of which a "characteristic gas" is excited. The absorption of the light brings about changes in temperature, the latter lead to an increase in volume, and this in turn leads to pressure fluctuations, which are detected as sound waves and are processed electronically. Gases and gas concentrations can be measured hereby. $N_2$ can also be detected.

A photoacoustic sensor is also described in M. El-Safoury: "Miniaturized photoacoustic detection of organofluorine-based refrigerants," *Journal of Sensors and Sensor Systems*, Vol. 9, Mar. 5, 2020, pp. 89-97.

A device and a process for the in-situ calibration of a photoacoustic sensor are described in DE 10 2016 216 875 A1. Calibration information that is obtained during the operation of the photoacoustic sensor is used for this purpose.

SUMMARY

A basic object of the present invention is to provide a photoacoustic sensor and a process for detecting at least one target gas with the use of a photoacoustic sensor, wherein the sensor can be handled more easily than prior-art photoacoustic sensors.

The object is accomplished by a photoacoustic sensor having the features of the device according to the invention and by a process having the process features according to the invention. Advantageous embodiments are described herein. Advantageous embodiments of the photoacoustic sensor are, insofar as meaningful, also embodiments of the process according to the present invention and vice versa.

The photoacoustic sensor according to the present invention and the process according to the present invention are capable of detecting at least one target gas in an area to be monitored. The target gas to be detected or at least one target gas to be detected is, in one application, an anesthetic or a solvent, and the area to be monitored is especially a closed room in a building or in a vehicle. The sensor and the process are preferably capable of measuring the concentration of at least one target gas in the area at least approximately.

A target gas wavelength range is predefined. The target gas to be detected or at least one target gas to be detected and preferably each target gas to be detected attenuates the intensity of electromagnetic waves, which pass through the target gas, at least in this target gas wavelength range. It is possible that a target gas also attenuates electromagnetic waves outside the target gas wavelength range.

The photoacoustic sensor according to the present invention comprises
  a radiation source,
  a sample chamber,
  a detection chamber and
  an acoustic receiver.

The process according to the present invention is carried out with the use of such a photoacoustic sensor.

The sample chamber is in fluid connection with the area that shall be monitored on the presence of at least one target gas to be detected and in which the target gas shall be detected—or for which the presence of such a target gas shall be ruled out. Thanks to the fluid connection, a gas sample from the area to be monitored can flow into the sample chamber. The sample chamber is capable of receiving this gas sample.

The detection chamber comprises a housing and an interior. The housing fluid-tightly encloses the interior. As a result, the interior is sealed against the environment of the detection chamber in a fluid-tight manner. "Fluid-tight" means tight for each fluid that may be present (occur) during a use in the environment of the sensor, or is contained in the detection chamber, possibly aside from at times unavoidable gaps. In particular, a gas mixture, which contains or may contain the target gas or a target gas, cannot enter into the detection chamber. Therefore, substantially no target gas can enter into the detection chamber together with the gas mixture, either.

The interior of the detection chamber is filled with a replacement gas. This replacement gas may be a mixture of different gases. Nevertheless, in the following the term "replacement gas" is used. It is possible that the concentration of the replacement gas in the detection chamber is equal to a typical or average or minimum detectable concentration of a target gas to be detected in the environment of the sensor. Since the detection chamber is sealed in a fluid-tight manner, no relevant quantity of replacement gas can escape from the detection chamber.

The radiation source is capable of emitting electromagnetic waves in the direction of the sample chamber. The wavelength range of the emitted electromagnetic waves comprises the predetermined target gas wavelength range. The sensor is configured such that emitted electromagnetic waves pass through the sample chamber and the detection chamber. Over the optical path, through which the electromagnetic waves travel, the sample chamber is located between the radiation source and the detection chamber. It is, of course, possible that a part of the electromagnetic waves flows past the sample chamber and/or past the detection chamber.

Electromagnetic waves, which pass through the detection chamber, elicit an acoustic effect in the detection chamber. This elicited acoustic effect results especially from the fact that the absorption by the replacement gas in the detection chamber reduces the radiation intensity of the electromagnetic waves and the absorption generates thermal energy, which in turn triggers the acoustic effect in the detection chamber. The acoustic effect is correlated with the intensity of the electromagnetic waves, which pass through the detection chamber. As a rule, the acoustic effect increases/becomes stronger with increasing radiation intensity.

The acoustic receiver is capable of measuring an indicator of the acoustic effect, which the electromagnetic waves elicit during their passage in the detection chamber. For example, the acoustic receiver measures the sound intensity and/or the sound volume of sound waves, which are generated by the acoustic effect in the detection chamber. The acoustic receiver is capable, furthermore, of generating a signal for the measured acoustic effect. The acoustic receiver is preferably configured as a microphone, or it comprises at least one microphone and optionally a plurality of spaced apart microphones.

According to the present invention, the detection chamber is free from the target gas to be detected or of each target gas to be detected. The detection chamber is filled rather with the replacement gas, which fills the interior of the detection chamber. The replacement gas possesses the following properties at least at an ambient temperature between 10° C. and 40° C.:

The replacement gas is chemically more inactive than the target gas or each target gas, ideally it is chemically inert.

The replacement gas attenuates electromagnetic waves in the target gas wavelength range similarly to the target gas to be detected or to each target gas to be detected. More precisely, the spectral overlap between the target gas or at least one and preferably each target gas and the replacement gas in the target gas wavelength range is above 0.2, preferably above 0.35, and especially preferably above 0.5.

The "spectral overlap" between a target gas and the replacement gas is defined as an indicator of the congruence between the spectral response of the transmission of the target gas and the spectral response of the transmission of the replacement gas in the target gas wavelength range. This indicator is standardized to the range between 0 and 1, in which the greater the congruence, the greater the indicator.

The transmission (transmission ratio) of a gas for electromagnetic waves is a number between 0 and 1, which indicates the percentage of the electromagnetic waves that passes through the gas, more precisely, how high the intensity of the waves still is after passing through the gas, compared to the intensity before passing through it. The transmission is related to defined operating conditions, especially to a defined path length of the electromagnetic waves through the gas of, e.g., 1 cm, and a defined concentration of the gas, e.g., 1 vol. %. If the gas does not absorb any waves at all, the transmission is 1. If the gas absorbs waves completely, the transmission equals 0. The transmission varies, as a rule, with the wavelength of the electromagnetic waves.

The dependence of the transmission on the wavelength is called "spectral response" of the transmission of the gas. The closer the congruence between the spectral response of the transmission of the replacement gas and the spectral response of the transmission of the target gas, the greater is the spectral overlap. In case of completely identical spectral responses (an only theoretical situation), the spectral overlap equals 1. If the target gas had a transmission of 0 and the replacement gas had a transmission of 1 in the entire target gas wavelength range (also a theoretical situation), the spectral overlap would be 0. Since the target gas causes a measurable attenuation of the intensity of electromagnetic waves in the target gas wavelength range, it is sufficient for the spectral overlap to refer to the target gas wavelength range only. The spectral responses outside the target gas wavelength range do not influence the spectral overlap.

The ambient temperature in a closed room (room temperature) is usually in the temperature range between 10° C. and 40° C. Frequently target gases, which may be harmful for humans, especially anesthetics and/or solvents, must be detected precisely in a closed room. The spectral overlap depends, as a rule, to a negligible extent on the ambient temperature.

The target gas or each target gas, which the photoacoustic sensor shall detect is predefined. As a result, a meaningful target gas wavelength range is known as well. If a target gas with a concentration above a detection threshold is present in the sample chamber, this target gas attenuates the intensity of the electromagnetic waves in the target gas wavelength range, while the electromagnetic waves are passing through the sample chamber. If no target gas with a concentration above the detection threshold is present, the waves are attenuated less intensely or not at all. This difference is due to the fact that the emitted electromagnetic waves comprise the target gas wavelength range.

A high spectral overlap between the target gas and the replacement gas is meaningful above all for the following reason: The entire transmission during the passage through the sample chamber and the detection chamber is the product of the transmission in the sample chamber and that in the detection chamber. If the two transmissions are approximately equal (high spectral overlap), the change in the acoustic effect, which is brought about by the target gas, can be measured with an especially high degree of reliability. The target gas can therefore be detected with a high level of certainty. This will be explained in more detail below.

The acoustic effect, which is elicited by the electromagnetic waves during their passage in the detection chamber, is correlated with the intensity of these electromagnetic waves. Over the beam path of the electromagnetic waves, the sample chamber is between the radiation source and the detection chamber. Since a target gas in the sample chamber reduces the intensity of the electromagnetic waves, the acoustic effect in the detection chamber is influenced by whether target gas is present in the area or not. Consequently, if the elicited acoustic effect is significantly weaker than in a reference state, in which no target gas is present in the sample chamber, a target gas is detected.

The higher the concentration of the target gas or of a target gas in the sample chamber, the weaker is, as a rule, the elicited acoustic effect. The indicator of the acoustic effect is thus correlated with the concentration of the target gas in the sample chamber, doing so preferably as follows: The weaker the acoustic effect, the higher is the concentration of the target gas.

The replacement gas, with which the detection chamber is filled, is chemically more inactive than the target gas to be detected or each target gas to be detected. In particular, the replacement gas is chemically more inactive with respect to a material that is present in the housing of the detection chamber or in another component of the sensor.

The process according to the present invention is carried out with the use of a photoacoustic sensor, which comprises a radiation source, a sample chamber, a detection chamber and an acoustic receiver. The detection chamber is sealed against the environment in a fluid-tight manner, it is free from the target gas to be detected or each target gas to be detected, and it accommodates a replacement gas. The detection chamber is preferably filled completely with the replacement gas. The replacement gas is chemically more inactive than the target gas to be detected or each target gas to be detected and has a relatively high spectral overlap with the target gas.

The process according to the present invention comprises the following steps:

A state is brought about, in which a gas sample flows from the area, which is to be monitored with respect to the target gas, into the sample chamber of the sensor.

The radiation source emits electromagnetic waves in the direction of the sample chamber.

At least a part of the emitted electromagnetic waves passes through the sample chamber and the detection chamber.

During their passage through the detection chamber, the electromagnetic waves elicit an acoustic effect in the detection chamber. This acoustic effect is correlated with the intensity of the electromagnetic waves, which pass through the detection chamber.

The acoustic receiver of the sensor measures an indicator of the acoustic effect, which is elicited by the electromagnetic waves in the detection chamber.

The acoustic receiver generates a signal for the measured acoustic effect.

The sensor according to the present invention is configured as a photoacoustic sensor and comprises an acoustic receiver. The process according to the present invention is carried out with the use of such a sensor. In some applications, a photoacoustic sensor has a number of advantages compared to other sensors, which are likewise capable of measuring the concentration of a target gas. One advantage is that the function of the photoacoustic sensor depends less on the reactivity of chemicals than, for example, the function of an electrochemical or passive chemical sensor. The sensor according to the present invention contains no chemical that reacts chemically with a target gas and is therefore consumed during operation. The detection chamber rather shields the replacement gas against the environment and thus against a target gas. The sensor according to the present invention has is less susceptible to cross sensitivities to foreign gases. The risk that a chemical escapes from the sensor is very low.

Another advantage of a photoacoustic sensor results from the fact that the measurement sensitivity of a sensor, in which light passes through a measured path, depends substantially on the length of the optical measuring path obtained. A sufficiently large optical measuring path must therefore be obtained, which requires either a large housing or at least one mirror. The optical path that can be obtained by a photoacoustic sensor is, by contrast, sufficiently long in any application even when no mirror is used at all, or only fewer mirrors are used than in other sensors. A mirror may become contaminated and/or it may corrode, and, in addition, moisture may condense on the mirror. The contamination as well as the corrosion and the condensation may distort measurement results. A photoacoustic sensor can therefore often be used for a longer time in a humid and/or dirty environment than other sensors with a light source, especially if the sensor according to the present invention has no mirror.

The sensor according to the present invention comprises an acoustic receiver, and optionally a plurality of acoustic receivers. It is not necessary for the sensor to comprise a photoelectric receiver, i.e., a receiver that generates an electrical signal depending on the intensity of impinging light beams. The measurement results of a photoelectric receiver could be distorted if interfering light falls on the receiver, for example, due to changing and/or intense ambient lighting. This drawback is avoided by a photoacoustic sensor. The housing of the detection chamber shields in many cases the interior of the detection chamber acoustically from the environment of the detection chamber, so that results of a photoacoustic sensor are not distorted in a relevant manner even by ambient noises.

Another advantage is in some applications that a photoacoustic sensor has a shorter response time than a sensor having another configuration. This advantage is achieved especially because a compact measured path can be obtained and no component of the sensor according to the present invention has to reach at first a defined operating temperature.

According to the present invention, the detection chamber is sealed against the environment in a fluid-tight manner. The detection chamber is therefore protected to a certain degree from moisture and other chemical and thermal environmental effects. Such environmental effects may likewise distort the results of the photoacoustic sensor.

In addition, no target gas can reach the fluid-tight detection chamber from the area to be monitored or from the sample chamber. In particular, a target gas cannot exert an undesired chemical effect on the acoustic receiver or react chemically with the replacement gas.

The replacement gas does not escape from the fluid-tight detection chamber, or it does so to a negligibly low extent only, so that the concentration of the replacement gas in the detection chamber remains constant over a long time period. The photoacoustic sensor according to the present invention therefore yields reproducible results, i.e., the elicited acoustic effect does not change substantially in the course of time at equal concentration of a target gas despite of a possible aging of the sensor. An advantageous embodiment described farther below makes it possible in many cases to compensate a potential aging, which is nonetheless possible up to a certain degree, by calculation without having to measure the aging directly.

According to the present invention, the detection chamber is free from the target gas to be detected or from each target gas to be detected. Many target gases to be detected, especially many anesthetics and solvents, are chemically corrosive. Therefore, in many cases they react with a material of the housing of the detection chamber or of another component of the photoacoustic sensor. In order for the electromagnetic waves to be able to pass through the sample chamber and the detection chamber, at least one respective window, which is enclosed by a seal, is frequently formed in both a housing of the sample chamber and in a housing of the detection chamber. A chemically corrosive target gas can cause in many cases this seal to become leaky, so that detection results may be distorted. Since the replacement gas is chemically more inactive, the risk that the replacement gas will damage a material is significantly lower.

Since no target gas is present according to the present invention in the detection chamber, a photoacoustic sensor according to the present invention can in many applications be manufactured, stored and handled more easily and it changes to a lesser extent in the course of time than does a photoacoustic sensor in which the detection chamber contains the target gas or a target gas. This is especially true of a chemically corrosive target gas.

In addition, some target gases to be detected change their state significantly depending on ambient conditions, especially on the ambient temperature, ambient humidity and/or depending on whether electromagnetic waves pass through the target gas or not. In addition, some target gases are chemically unstable, so that the spectral characteristic of a target gas changes in the course of time in the detection chamber. Since the photoacoustic sensor in the detection chamber has no target gas, the absorption characteristic of the gas in the detection chamber changes to a lesser extent due to changing ambient conditions and in the course of time. In many cases, a photoacoustic sensor according to the present invention therefore needs to be adjusted only once prior to the first use and only at longer time periods or not at all thereafter. The sensor according to the present invention therefore, in many cases, can be handled and used more easily than a photoacoustic sensor in which a target gas is contained in the detection chamber.

According to the present invention, the detection chamber is filled with a replacement gas. This replacement gas attenuates electromagnetic waves in the target gas wavelength range at a similar intensity as the target gas to be detected or as at least one target gas to be detected. More precisely, the spectral overlap between the target gas and the replacement gas in the target gas wavelength range is above 0.2. A high spectral overlap has especially the following advantage: If the target gas to be detected or a target gas to be detected is present in the sample chamber above a detection threshold, the emitted electromagnetic waves in the target gas wavelength range are already attenuated considerably in the sample chamber. The detection chamber is located downstream of the sample chamber in the beam path between the radiation source and the acoustic receiver. The detection chamber with the replacement gas is therefore quasi in the electromagnetic shadow, wherein the sample chamber with the target gas produces this shadow. Therefore, only a weak acoustic effect is generated in the detection chamber. If, by contrast, no target gas is present in the sample chamber, the detection chamber is not in the electromagnetic shadow of the sample chamber and the acoustic effect is stronger.

If the acoustic overlap between the target gas to be detected and the replacement gas in the detection chamber is high enough, the difference between the acoustic effect in the presence of the target gas and the acoustic effect in the absence of the target gas in the sample chamber is sufficiently high. A sufficiently high acoustic overlap therefore leads to a relatively good detection performance of the sensor according to the present invention. A target gas is detected with a high level of reliability and the sensor generates only relatively few false alarms.

A photoacoustic sensor according to the present invention achieves in many cases an approximately equal sensitivity during the detection of a target gas as a photoacoustic sensor, in which the detection chamber is also filled with a target gas or with a mixture of a target gas and another target gas. However, the photoacoustic sensor according to the invention avoids the just described drawbacks of a corrosive and/or unstable target gas in the detection chamber.

The target gas to be detected or each target gas to be detected attenuates the intensity of electromagnetic waves in the target gas wavelength range. Thermal energy is, as a rule, released during this attenuation. Some target gases therefore change their state of aggregation from liquid to gaseous at room temperature when electromagnetic waves pass through the target gas. If the detection chamber contained such a target gas, the results of the photoacoustic sensor would not be sufficiently reliable in some cases, or the response time would be too long. By contrast, the replacement gas is gaseous at least at an ambient temperature between 10° C. and 40° C., i.e., at room temperature. This gaseous state of the replacement gas is present if no electromagnetic waves pass through the detection chamber, for example, because the sensor is switched off. The gaseous state is also present if no target gas to be detected is present in the sample chamber and electromagnetic waves are therefore attenuated only slightly or not at all in the sample chamber and thus, they reach and pass through the detection chamber with the highest intensity possible.

Some target gases to be detected are chemically unstable. If the detection chamber contained such an unstable target gas, the target gas in the detection chamber would change its absorption characteristic significantly in the course of time. Such a photoacoustic sensor would have to be adjusted more frequently. The replacement gas of the photoacoustic sensor according to the present invention is, by contrast, preferably chemically more stable than the target gas to be detected or each target gas to be detected, so that the sensor according to the present invention in many cases needs to be adjusted less frequently.

Many target gases to be detected, especially anesthetics and solvents, attenuate the intensity of electromagnetic waves especially strongly in a wavelength range of 7 µm to 10 µm. The target gas wavelength range of the sensor preferably therefore comprises this range from 7 µm to 10 µm, or particularly the range from 8 µm to 9 µm.

The sensor shall be able to detect a target gas with a high level of reliability. In addition, it is desirable that the sensor generates as few false alarms as possible and ideally no false alarms at all, i.e., that it should detect a target gas when in reality no target gas is present as rarely as possible. It is therefore desirable that the electromagnetic waves elicit a sufficiently strong acoustic effect in the detection chamber at least when no target gas is present in the sample chamber. It is only in this case that an attenuation or another change based on the target gas can be detected with sufficient certainty. In one embodiment, the replacement gas in the detection chamber is a gas mixture of a gas that has a high spectral overlap with the target gas to be detected or with a target gas to be detected and a diluting gas, which reduces the intensity of electromagnetic waves only slightly or not at all in the target gas wavelength range. More precisely, the diluting gas has a transmission above 0.9, preferably above 0.95 and especially preferably above 0.99 in the entire target gas wavelength range. This gas mixture has on the whole, the high spectral overlap according to the present invention with the target gas. Thanks to the diluting gas, the intensity of the electromagnetic waves is reduced to a lesser extent in the detection chamber as compared to no diluting gas being added. The addition of a diluting gas makes it therefore easier in many cases to adapt the acoustic receiver to the intensity of the sound waves that are generated by the acoustic effect. Also, in some cases the addition of the diluent gas reduces the limit of detection for the target gas.

In one embodiment, the replacement gas comprises a partially fluorinated hydrocarbon, especially tetrafluoroethane or heptafluoropropane. Such a hydrocarbon absorbs the emitted electromagnetic waves in the target gas wavelength range in approximately the same manner (spectral overlap above 0.2) as some target gases, especially anesthetics or solvents. These hydrocarbons possess the desired properties, are in particular chemically relatively stable, and can therefore be handled more easily than anesthetics or solvents.

The photoacoustic sensor according to the present invention comprises at least one acoustic receiver, which is capable of measuring the elicited acoustic effect. In one embodiment, the sensor comprises a plurality of acoustic receivers, which are capable of measuring the same indicator or even different indicators for the acoustic effect and/or which employ different measurement methods. Each acoustic receiver is capable of generating a respective signal each for the measured acoustic effect. This embodiment creates redundancy. This configuration increases in many cases the sensitivity of the sensor, especially if the same sensor shall detect different target gases.

In one embodiment, the sensor additionally comprises a reference receiver. This reference receiver is capable of measuring an indicator of the intensity of the electromagnetic waves, which pass through the detection chamber, and of generating a signal for the measured intensity. The reference receiver is capable of measuring this indicator in a reference wavelength range. This reference wavelength range is disjunct from the target gas wavelength range. The target gas or each target gas has a high transmission, preferably a transmission greater than or equal to 0.9, in the reference wavelength range. The signal of the reference receiver is therefore independent from or depends only insignificantly on whether a target gas is present in the sample chamber or not. The reference receiver may comprise, in particular, a photoelectric or an acoustic receiver.

However, the signal of the reference receiver depends on at least one of the following factors, which may influence a detection result of the photoacoustic sensor according to the present invention:

- on the transmission power of the radiation source, which may decrease in the course of time based on wear, may vary based on contamination and may, in addition, depend on the available electrical voltage, and the electrical voltage may vary especially if the sensor has a voltage supply unit of its own or if the line voltage in a stationary power supply network fluctuates,
- on condensation of moisture on a window of the detection chamber or of the sample chamber, wherein the electromagnetic waves pass through this window and wherein the condensation may lead to an absorption of electromagnetic waves and thereby mimic a higher concentration of the target gas,
- on condensation on an optional mirror, which extends the optical path, and
- on contamination or scratching of such a window.

The signal of the reference receiver can be used to compensate the influence of the factors just mentioned on the signal of the acoustic receiver by calculation. For example, the signal of the acoustic receiver is multiplied by a correction factor, and the lower the signal of the reference receiver, the higher is this correction factor. Thanks to the reference receiver, the photoacoustic sensor is even less sensitive to aging and to changing ambient conditions.

According to the present invention, the acoustic receiver generates a signal for the measured acoustic effect. The optional reference receiver just described generates a signal for the intensity of the electromagnetic waves in the detection chamber. The sensor preferably comprises, furthermore, a data-processing analysis unit. The analysis unit receives the signal from the acoustic receiver and optionally the signal from the reference receiver, it analyzes the received signal or each received signal and it decides automatically whether the target gas to be detected or at least one target gas to be detected is present in the sample chamber at a concentration above a detection threshold or not. A target gas concentration above the detection threshold causes a change in the measured acoustic effect in a measurable manner compared to a lower concentration or the absence of target gas.

The analysis unit optionally decides whether a target gas is present with a concentration above a predefined concentration threshold or not in the sample chamber. This concentration limit is predefined, for example, by a legal regulation. A concentration above the concentration limit causes a significant change in the acoustic effect and it attenuates the acoustic effect, for example, significantly. At a concentration above the concentration limit, the analysis unit preferably causes an alarm to be outputted in a form perceptible by a person. In one embodiment, the sensor itself outputs this alarm. In another embodiment, the sensor transmits a message to a receiver located remotely in space, and the receiver outputs the alarm.

The analysis unit preferably determines the concentration of the target gas or one target gas in the sample chamber. The analysis unit in this case uses the fact that the change, for example, attenuation, of the acoustic effect measured in the detection chamber is correlated with the concentration of the target gas in the sample chamber. The analysis unit has read access to a memory, in which a computer-evaluable concentration relationship is stored for at least one target gas. This concentration relationship describes a dependence between the concentration of this target gas in the sample chamber and the measurable indicator of the acoustic effect elicited in the detection chamber.

In order to determine the concentration of the target gas in the sample chamber, the analysis unit applies the stored concentration relationship to the signal for the measured acoustic effect.

In a variant of this configuration, the sensor according to the invention is capable of measuring the respective concentrations of at least two target gases. A user selects a target gas, whose concentration shall be measured. The sensor comprises for this purpose a selection unit, which a person can use to select a target gas. A respective concentration relationship is stored for each selectable target gas in the memory. The analysis unit determines the concentration of the selected target gas. The analysis unit applies for this purpose the concentration relationship that is associated with the selected target gas to the signal for the measured acoustic effect.

The concentration relationship or each concentration relationship is preferably determined empirically in advance in a calibration phase and is stored. Different values are established for the concentration of the target gas to be detected or for each target gas to be detected in the sample chamber one after another during this calibration phase, and the indicator of the acoustic effect brought about now is then measured for each established concentration.

In one embodiment, this concentration relationship is valid for the entire temperature range, in which the temperature of the gas mixture to be tested may be. If the sensor is used in a closed room, this temperature range is in the range of the usual room temperature, preferably between 10° C. and 40° C. In another embodiment, at least two different temperature ranges are determined empirically and stored. In one embodiment, the sensor comprises a thermometer, which measures the temperature of the gas mixture, or the temperature in the vicinity of the sensor, and the analysis unit selects the concentration relationship that belongs to the temperature range, into which the measured temperature falls.

In another variant of this configuration, the sensor determines the respective concentration of each target gas, to which a concentration relationship is assigned in the memory, for each target gas one after another or overlapping in time. The analysis unit applies one after another each stored concentration relationship to the measured value of the indicator of the acoustic effect produced. This yields a respective concentration for each target gas to which a concentration relationship is assigned in the memory. This configuration makes it possible to generate an alarm at an excessively high concentration of a target gas without a user having necessarily to select a target gas beforehand and without the sensor necessarily outputting a message of which target gas has an excessively high concentration. This embodiment eliminates the need especially for a selection unit. With a suitable replacement gas in the detection chamber, the sensor according to this embodiment is capable of monitoring especially a closed room for a plurality of anesthetics or solvents, which may be present in that room.

These two configurations may be combined with one another. For example, the sensor may optionally be operated in a manual mode, in which a user selects at first a target gas by means of the selection unit and the sensor applies the concentration relationship to the selected target gas, or in an automatic mode, in which the sensor applies each stored concentration relationship one after another.

Furthermore, a reference relationship is preferably stored in the memory. This reference relationship specifies the above-described correction factor as a function of a signal of the reference receiver.

In one embodiment, the analysis unit determines an uncorrected concentration of the target gas or at least one target gas as a function of the measured indicator of the acoustic effect. "Uncorrected" means that the influence of one of the factors, which were mentioned above in connection with the reference receiver, has not been corrected for the measured concentration. Depending on a signal of the reference receiver, the analysis unit determines a correction factor. The lower the signal of the reference receiver is, the higher is this correction factor. The analysis unit applies the correction factor to the determined, uncorrected concentration, for example, by multiplication. For example, the correction factor is the reciprocal value of the current signal value from the reference receiver, and the uncorrected concentration is divided by this signal value. The application yields the concentration to be determined.

In one embodiment, the photoacoustic sensor according to the present invention is configured as a portable device, which a person can carry with him/her for example, can attach it to their clothing. The analysis unit is preferably a part of this portable device. This sensor preferably comprises an output unit, which is capable of outputting an alarm for the presence of a target gas, or it can output a measured concentration of a target gas in a form perceptible for a person. In addition, this sensor comprises a power supply unit of its own.

In another configuration, the photoacoustic sensor according to the present invention is mounted stationarily. A plurality of photoacoustic sensors are preferably mounted at different locations of a room to be monitored. In a preferred configuration, the optional data-processing analysis unit is arranged in a center located remotely in space. The photoacoustic sensor or each photoacoustic sensor transmits the signal for the measured acoustic effect and optionally the signal from the reference receiver to a receiver in this center, doing so in a wireless or wired manner. An output unit of the central receiver outputs an alarm or a measured target gas concentration, preferably together with position information, which specifies the position of the sensor that has detected a target gas or a high target gas concentration. This configuration eliminates the need for having to mount a plurality of sensors with a respective analysis unit each in the room itself.

In one application, a photoacoustic sensor according to the present invention is used to detect at least one anesthetic or a solvent in a closed room. The target gas wavelength range comprises the range from 7 μm to 10 μm. Many anesthetics and solvents, which are to be detected, absorb electromagnetic waves in this wavelength range.

It is also possible that the photoacoustic sensor is a mobile device, and the evaluation unit is part of a stationary receiver.

The present invention will be described below on the basis of exemplary embodiments. In the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 4 is a graph showing two exemplary concentration relationships between the anesthetic concentration and the reduction of the sound intensity for two different anesthetics.

DESCRIPTION OF PREFERRED EMBODIMENTS

The sensor according to the present invention is used in the exemplary embodiment to measure the concentration of at least one anesthetic and/or at least one solvent in the ambient air in a closed room, in which people may be present. The room is, for example, a recovery room or an operating room or also a storage room in a hospital or in a vehicle or in a hall of a production plant or warehouse. The sensor shall at least decide automatically whether the concentration of the anesthetic or solvent is above or below a predefined limit. This limit is predefined, for example, by legal regulations for the safety of workplaces and is, for example, between 5 ppm and 200 ppm (parts per million) and is stated, as a rule, in ppm, mL/^3 or volume percent.

Figure 1:
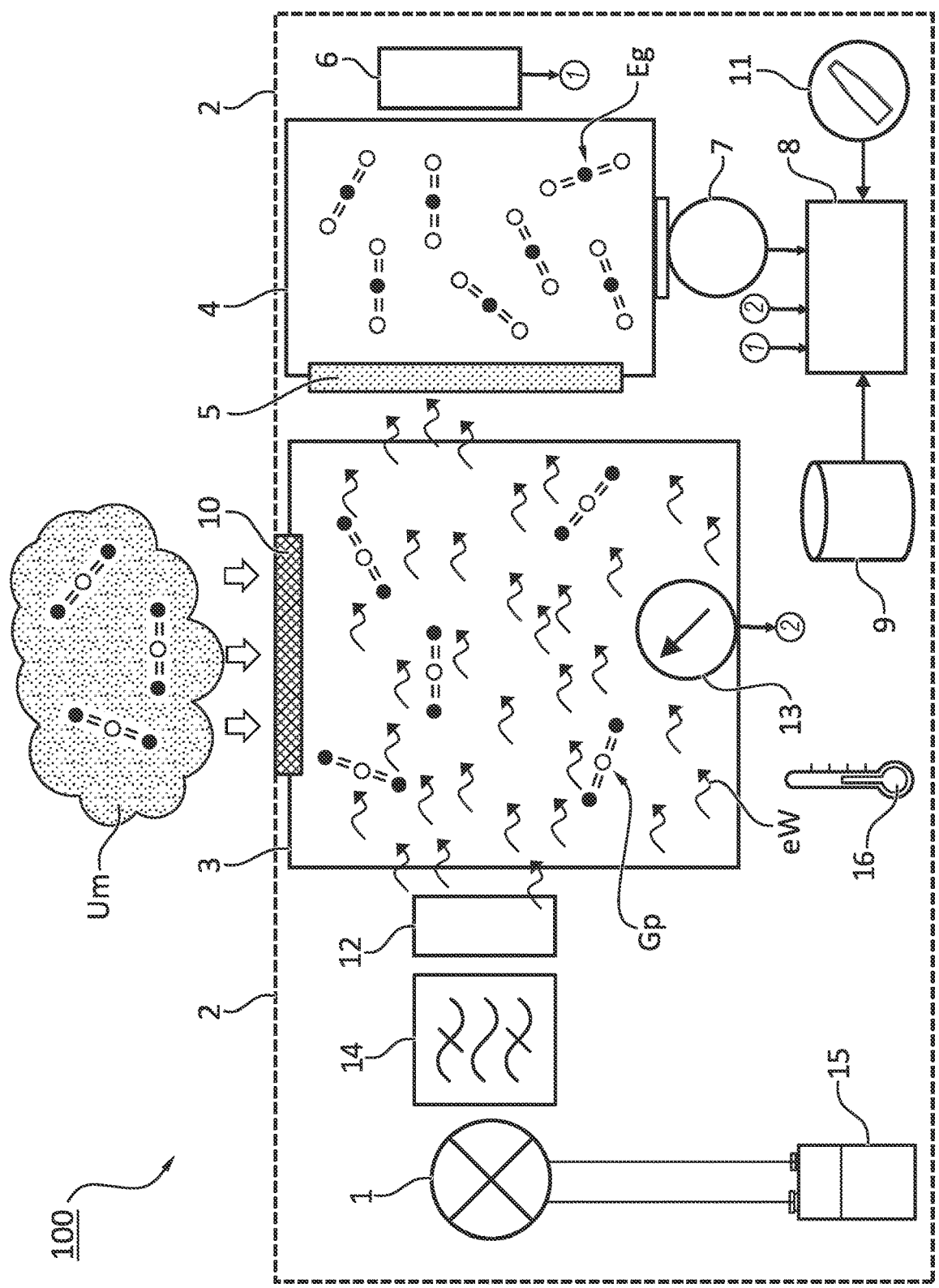
FIG. 1 is a schematic view showing a photoacoustic sensor according to the present invention during use.

FIG. 1 shows schematically the photoacoustic sensor 100 according to the exemplary embodiment during a use as well as the environment Um as the area that the sensor 100 shall monitor. The sensor 100 may be configured as a portable device, which a person carries along with them, while the person is present in a possibly contaminated room, or it may be mounted on a wall of a room or on a medical device or in a production plant.

In one configuration, the sensor 100 comprises a power supply unit 15 (shown schematically) of its own, especially a plurality of rechargeable batteries. The sensor 100 can preferably be brought into a measuring state and into a resting state. The sensor 100 is capable of detecting anesthetics and solvents in the measuring state, and the sensor 100 consumes less electrical energy in the resting state. The sensor 100 is preferably capable of providing measured values after a response time, which is preferably between 10 sec and 1 minute, after the sensor 100 has been switched over into the measuring state.

The photoacoustic sensor 100 has the following components:

A radiation source 1, which emits electromagnetic waves,
an optical or electronic band pass filter 14,
a modulator 12,
a sample chamber 3, which contains a sample Gp of gas to be tested, of ambient air to be tested in the exemplary embodiment,
an inlet 10 to the sample chamber 3, through which a gas sample Gp from the environment Um can enter into the sample chamber 3,
a detection chamber 4, which is separated from the environment Um and from the sample chamber 3 in a fluid-tight manner and contains a replacement gas Eg described farther below,
an optically transparent and fluid-tight window 5 in front of the detection chamber 4,
an acoustic receiver in the form of a microphone 7, which is in an acoustic connection with the detection chamber 4,
a reference receiver 6, which is likewise in an acoustic or optical connection with the detection chamber 4,
a pressure sensor 13, which measures an indicator of the gas pressure in the sample chamber,
an optional thermometer 16, which measures the temperature in the sample chamber 3,
a memory 9,
a data-processing analysis unit 8, which receives signals from the microphone 7 and from the reference receiver 6 and has read access to the memory 9 at least from time to time,
a switch 11,
a power supply unit 15 in the form of rechargeable batteries (storage batteries) and
a housing 2, which encloses the above-described components.

A filter permeable to gas in the inlet 10 prevents dust particles and moisture from entering into the sample chamber 3.

In one configuration, ambient air, which may contain at least one anesthetic to be detected, diffuses from the environment Um through the inlet 10 into the sample chamber 3. In another configuration, a pump, not shown, sucks air from the environment Um and delivers it thereby into the sample chamber 3.

The radiation source 1 emits electromagnetic waves eW in the infrared range in the direction of the sample chamber 3. The radiation source 1 preferably has a sufficiently small thermal mass for achieving a sufficiently high frequency during the modulation described below. In one configuration, the radiation source 1 is configured as a diaphragm radiator. It is also possible that the radiation source 1 is configured as a semiconductor laser.

The range of 7 μm to 10 μm is used as the target gas wavelength range in the exemplary embodiment. The emitted electromagnetic waves eW include this target gas wavelength range. The band pass filter 14 allows in one configuration only electromagnetic waves in this target gas wavelength range to pass through, and it additionally allows wavelengths in a reference wavelength range to pass through in another configuration.

The specification of the target gas wavelength range is a compromise between the following two requirements:

The photoacoustic sensor 100 shall detect a target gas with a higher level of reliability (narrow target gas wavelength range is desired), and electromagnetic waves with a sufficient intensity shall still reach the detection chamber 4 (broad target gas wavelength range is desired).

The modulator 12 causes the emitted electromagnetic waves eW to be pulsed. In one configuration, the modulator 12 modulates the voltage of the electrical current, with which the radiation source 1 is supplied. For example, the radiation source 1 is switched on and off in an oscillating manner. Because of the thermal inertia of the radiation source 1, a frequency of up to 15 Hz can be reached, as a rule, by this electrical modulation. The modulator 12 modulates the waves from the radiation source 1 mechanically in another configuration, for example, by means of a rotating mirror or a mirror moved in another manner, which alternatingly deflects electromagnetic waves eW to the sample chamber 3 and in another direction, or with a movable diaphragm, screen or perforated disc. A modulation frequency in the kHz range can be achieved in this manner. Many microphones have a high acoustic sensitivity precisely in the kHz range.

The pulsed electromagnetic waves eW pass through the sample chamber 3 and then through the detection chamber 4. The electromagnetic waves eW reach molecules in the fluid-tight detection chamber 4 and bring about a short-term local increase in temperature based on the pulses. This temperature rise leads to pressure waves in the detection chamber 4. The microphone 7 records these pressure waves and generates an electrical signal, which depends on the sound intensity of the pressure waves generated. This signal is correlated with the partial pressure as well as with the density of the gas in the sample chamber 3. The partial pressure and the gas density are known to be linked with one another based on the ideal gas law.

The signal from the microphone 7 is transmitted to the analysis unit 8. In addition, the signal from the pressure sensor 13 is transmitted to the analysis unit 8. The analysis unit 8 calculates the quotient from the signal for the gas density and the signal for the total pressure. This quotient is correlated with the concentration being sought.

The acoustic effect, which is brought about in the detection chamber 4, may depend not only on the concentration of a target gas in the sample chamber 3, but also on the temperature in the sample chamber 3. The optional thermometer 16 measures the temperature in the sample chamber 3. Depending on a signal of the thermometer 16, the influence of the temperature on the acoustic effect produced is compensated by calculation. As a result, the cross sensitivity of the sensor 100 to the ambient temperature is reduced significantly.

The concentration of at least one anesthetic shall be measured in the environment Um in the application example. It shall at least be determined whether this concentration is above a predefined concentration limit or not. The anesthetics usually used absorb a considerable part of electromagnetic waves eW in a defined range, which is predefined for the sensor 100 and it will hereinafter be called the "target gas wavelength range" WZB. The target gas wavelength range is, for example, the range from 7 μm to 10 μm or also the range from 6.5 μm to 15.5 μm in the exemplary embodiment.

Figure 2:
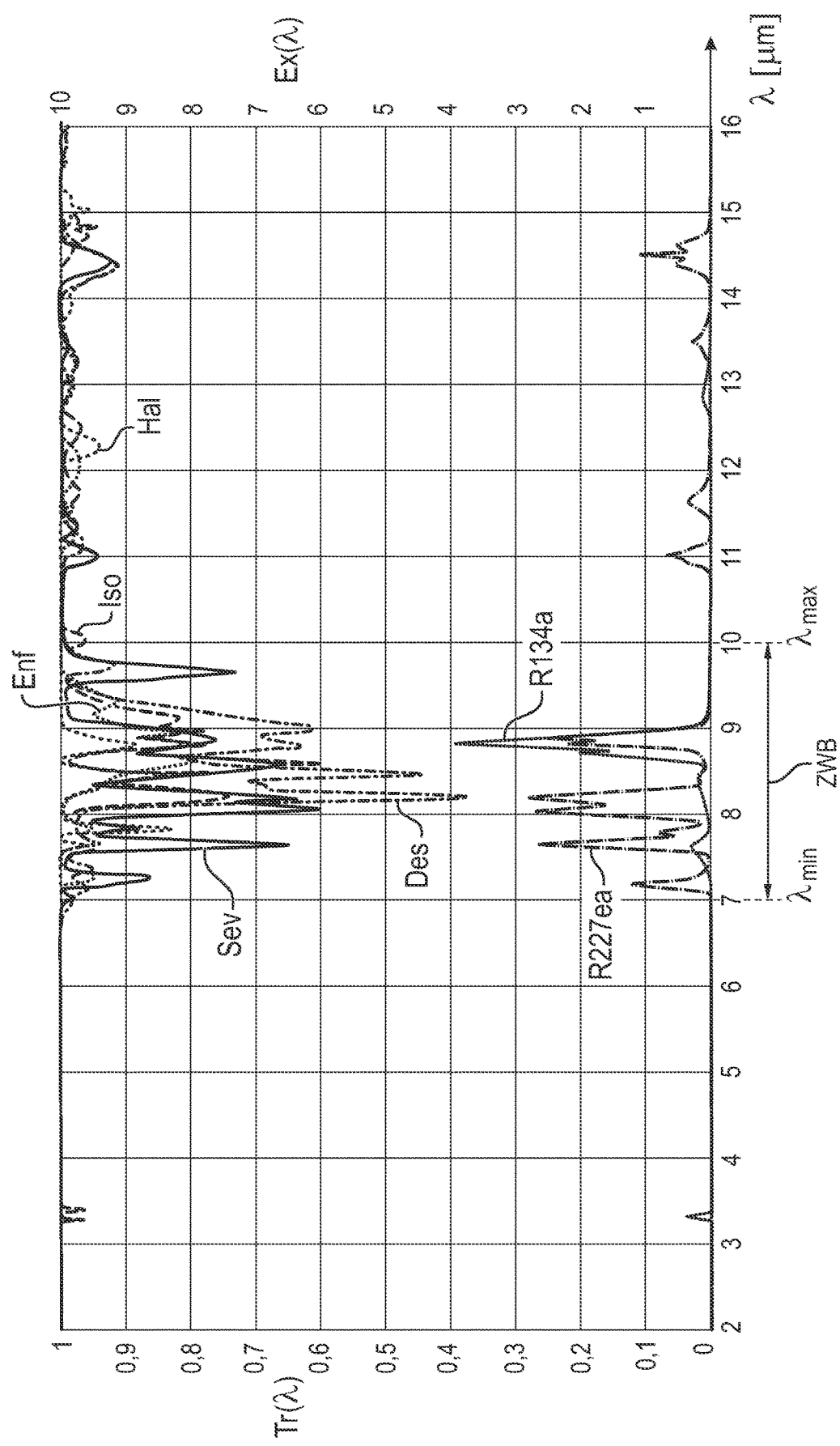
FIG. 2 is a graph showing the transmission of different anesthetics as well as the extinction (absorption intensity, degree of absorption) of different replacement gases as a function of the wavelength.
Figure 3:
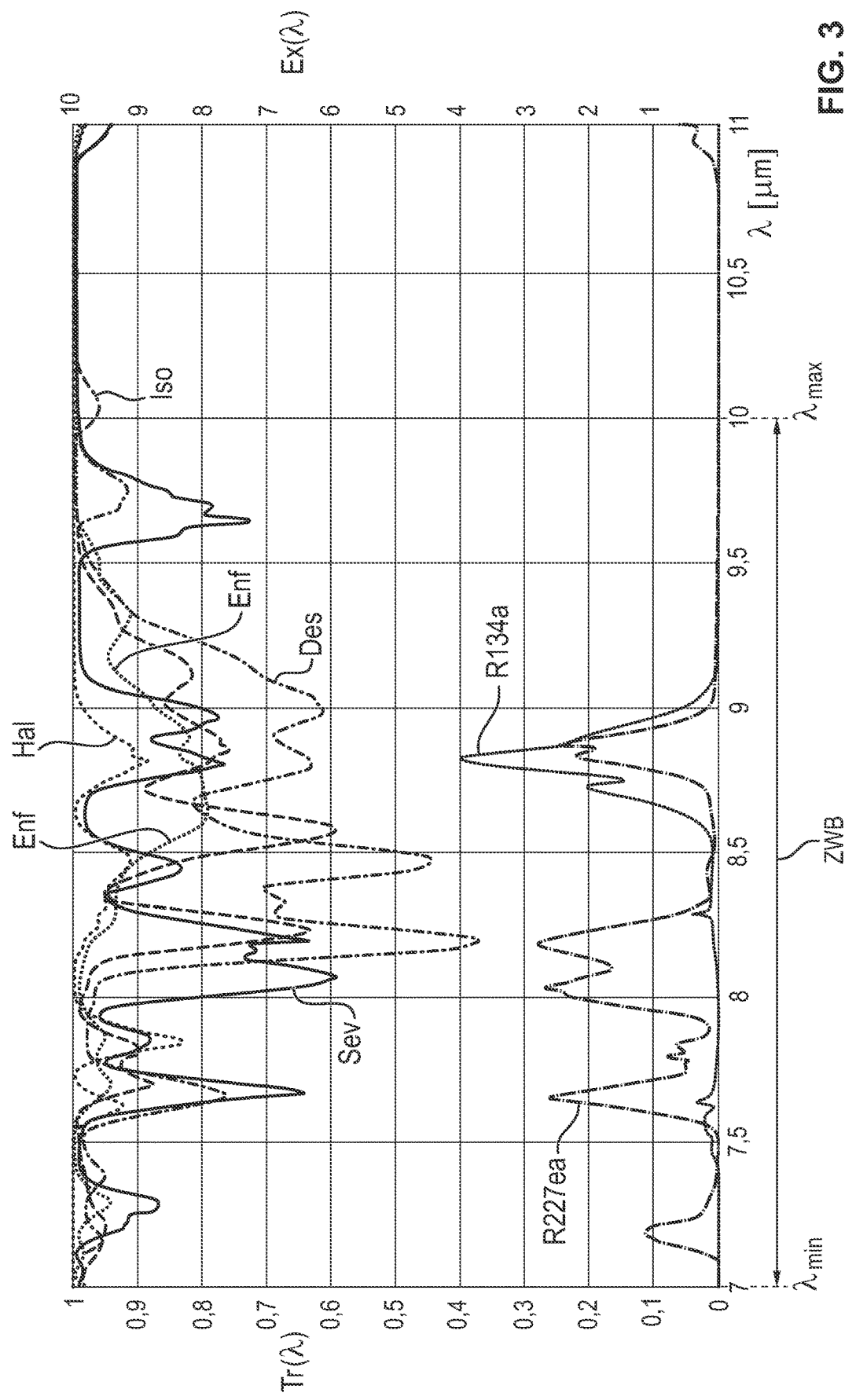
FIG. 3 is a detail of the view shown in FIG. 2.

FIG. 2 and FIG. 3 show at the top the transmission Tr of five different common anesthetics as a function of the wavelength λ, namely, Sevoflurane (Sev),
Desflurane (Des),
Halothane (Hal),
Isoflurane (Iso), and
Enflurane (Enf).

The wavelength λ in micrometers is plotted on the x axis of FIG. 2 and FIG. 3, FIG. 2 showing the wavelengths from 2 μm to 16 μm and the enlarged detail from FIG. 3 shows the wavelengths in the range of 7 μm to 11 μm. In addition, the target gas wavelength range ZWB of the exemplary embodiment is shown, namely, from a lower limit $\lambda_{min}=7$ μm to the upper limit $\lambda_{max}=10$ μm.

The radiation intensity of the part of the electromagnetic waves, which passes through a chamber containing the particular gas in question, relative to the radiation intensity of the electromagnetic waves which reach this chamber is designated by the term "transmission." The transmission Tr is a number between 0 and 1 or also between 0% and 100% and it depends on the wavelength λ of the electromagnetic waves. The transmission Tr is related in the exemplary embodiment to an optical path length of 1 cm and to a concentration of 1 vol. %. A scale for the transmission Tr(λ) is plotted on the left-handy axis of FIG. 2 and of FIG. 3. FIG. 2 and FIG. 3 show the respective spectral responses of the five anesthetics.

The bottom parts of FIG. 2 and FIG. 3 show the spectral responses of the extinction Ex (absorption intensity, degree of absorption) of two possible replacement gases, namely, the propellant R134a (tetrafluoroethane, $C_2H_2F_4$) and the propellant R227ea (heptafluoropropane, $C_3HF_7$). The extinction Ex also depends on the wavelength λ. A scale for the extinction Ex(λ) is plotted on the y-axis on the right.

The extinction Ex is an indicator of how intensely a gas absorbs and hence attenuates electromagnetic waves. The extinction Ex is a number greater than or equal to 0. The relation $Tr(\lambda)=e^{-Ex(\lambda)}$ exists between the transmission Tr(λ) and the extinction Ex(λ). The five anesthetics Sev, Enf, Hal, Des, Iso bring about a relevant extinction Ex(λ) in the target gas wavelength range ZWB.

The emitted electromagnetic waves eW preferably likewise include waves in the target gas wavelength range ZWB from 7 μm to 10 μm or in a range that comprises the target gas wavelength range ZWB. Thanks to the band pass filter 14, only electromagnetic waves in the target gas wavelength range ZWB and optionally in a reference wavelength range reach the sample chamber 3. Each of the five anesthetics in FIG. 2 and FIG. 3 reduces the intensity in the sample chamber 3 based on the extinction Ex and therefore also the local temperature rise, which is generated in the detection chamber 4 by the electromagnetic waves eW. If an anesthetic is present in the sample chamber 3, the microphone 7 measures a lower sound intensity in the detection chamber 4 compared to a gas sample in the sample chamber 3 that is free from anesthetics. In general, the higher the anesthetic concentration in the sample chamber 3, the lower is the sound intensity measured by the microphone 7 in the detection chamber 4. This acoustic effect is utilized to measure the anesthetic concentration being sought in the gas sample Gp or at least to decide whether the concentration is above or below a limit or whether an anesthetic is present above a detection limit.

As can also be seen in FIG. 2 and FIG. 3, the five common anesthetics reduce the intensity of the electromagnetic waves eW to the greatest extent in the range ZWB from 7 μm to 10 μm and to the lowest extent in other ranges, in which harmonics appear. Furthermore, it can be seen that the anesthetics absorb waves eW differently as a function of the wavelength λ. The sensor 100 according to the present invention is nevertheless capable of detecting all five anesthetics. A preferred configuration of how this is achieved will be described below.

The sensor 100 is calibrated in advance. At least one sample each with a defined and therefore known concentration of an anesthetic is delivered one after another into the sample chamber 3 during the calibration. Electromagnetic waves eW are emitted. The sound intensity, which is measured by the microphone 7, is measured. This is carried out for different concentrations. The higher the concentration of the anesthetic, the lower is the measured sound intensity. A functional concentration relationship is determined in this manner during the calibration for the anesthetic between the concentration in the sample chamber 3 and the sound intensity in the detection chamber 4. This is carried out for each anesthetic that shall be detected. For example, five different functional concentration relationships are determined empirically in this manner for the five anesthetics from FIG. 2 and FIG. 3. These functional concentration relationships are stored in the memory 9. FIG. 4 shows as an example two such functional concentration relationships, which should the understood to be illustrations only. The concentration of the anesthetic in the gas sample in volume percent is plotted on the x-axis, and the relative sound intensity is plotted on the y-axis, wherein the maximum 1 is related to a gas sample Gp free from anesthetic in the sample chamber 3.

The signal of the microphone 7, at the detection chamber 4, depends on the total pressure in the sample chamber 3, and the pressure sensor 13 measures this pressure. It is ensured in one embodiment that the total pressure remains constant during this calibration. The pressure sensor 13 measures the total pressure during the calibration as well in another embodiment. The predefined concentrations with the signal from the pressure sensor 13 are corrected by calculation, for example, by the measured partial pressure/the measured gas density being divided by the measured total pressure.

During a subsequent use, a user selects in one embodiment the anesthetic that shall currently be detected by means of the switch 11 shown schematically (cf. FIG. 1). By a read access to the memory 9, the analysis unit 8 inputs the functional concentration relationship, which belongs to this selected anesthetic. The analysis unit 8 receives signals from the microphone 7 as well as from the reference receiver 6 and optionally from the pressure sensor 13. The analysis unit 8 applies the inputted functional concentration relationship to the signal from the microphone 7 and thereby determines the corresponding concentration of the selected anesthetic in the gas sample Gp, which is present in the sample chamber 3.

The reference receiver 6 generates a signal, which depends on the intensity of the electromagnetic waves in a reference wavelength range. This reference wavelength range is disjunct from the target gas wavelength range ZWB and begins, for example, at a wavelength of 10 µm. All five anesthetics have a transmission greater than 0.9 in this reference wavelength range. The signal of the reference receiver 6 does not therefore depend on the concentration of a target gas in the detection chamber 3. The reference receiver 6 may likewise comprise a microphone or a photoelectric sensor.

In a preferred configuration, the analysis unit 8 determines an uncorrected value for the gas concentration by applying the functional concentration relationship to the value for the sound intensity, which the microphone 7 has measured. Depending on at least one signal value of the reference receiver 6 and optionally of at least one signal value of the pressure sensor 13, the analysis unit 8 calculates a correction factor. The lower the current value of the signal of the reference receiver 6, the higher is this correction factor. A low signal value results from a declining intensity of the radiation source 1 and/or from a contamination of a window, for example, because of condensed water droplets or dust or because the electrical voltage is becoming lower. The analysis unit applies the correction factor to the uncorrected concentration value, for example, by multiplication. Or else the analysis unit 8 divides the uncorrected value for the gas concentration by a signal value of the reference receiver 6, wherein the uncorrected value and/or the signal value are preferably standardized in a suitable manner.

The switch 11 is eliminated in another embodiment. Or else the sensor 110 comprises a switch 11, but it can also be operated in a mode in which the switch 11 is not needed. The analysis unit 8 applies one after another each functional concentration relationship, which is stored in the memory 9, to a value for the sound intensity, which the microphone 7 has measured. The analysis unit 8 calculates thereby a respective concentration for each anesthetic, to which a concentration relationship is assigned in the memory 9. The analysis unit 8 preferably calculates an uncorrected value for the gas concentrations and a correction factor each in this configuration as well.

An output unit of the sensor 100, which output unit is not shown, outputs the measurement result or each measurement result in a form perceptible by a person, for example, as a numerical value. Or else an alarm unit of the sensor 100, which alarm unit is likewise not shown, outputs an alarm in a form perceptible by a person when a concentration of the anesthetic or at least one anesthetic is detected above a predefined limit.

The electromagnetic waves eW pass through the sample chamber 3 and the window 5 and then enter into the detection chamber 4. In one configuration, which eliminates or complements the band pass filter 14, this window 5 is fully permeable to electromagnetic waves in the target gas wavelength range ZWB, i.e., in the wavelength range between 7 µm and 10 µm in the exemplary embodiment, and it absorbs electromagnetic waves outside the target gas wavelength range ZWB or outside a larger wavelength range, for example, outside the range of 6.5 µm to 15.5 µm, which comprises the reference wavelength range. Thanks to the band pass filter 14 or to the absorbing window 5, a cross sensitivity of the sensor 100 especially to water vapor and carbon dioxide ($CO_2$) is reduced. The wavelength spectrum of a target gas to be detected as well as that of the replacement gas Eg, with which the detection chamber 4 is filled, has only a slight overlap with the wavelength spectrum of water vapor and carbon dioxide ($CO_2$), which frequently occur in an environment of the sensor 100, and the undesired cross effect is therefore weak.

Mirrors are preferably arranged in the sample chamber 3 and/or in the detection chamber 4. These mirrors increase the optical path from the radiation source 1 to the receiver (microphone 7). If the length of the sample chamber 3 is a few cm, an optical length of several dm or even several m can be obtained.

The electromagnetic waves eW, which pass through the detection chamber 4, reach in the exemplary embodiment not only the microphone 7, but additionally the reference receiver 6 as well. This reference receiver 6 measures the intensity of electromagnetic waves eW in a wavelength range that is within the wavelength range that can pass through the band pass filter 14 or through the window 5, but outside the target gas wavelength range ZWB. For example, the reference receiver 6 measures the radiation intensity in the wavelength range of 10 µm to 11 µm. Because of the band pass filter 14 and/or the absorbing window 5, the signal of the reference receiver 6 depends only slightly, and ideally not at all, on the concentration of the anesthetic or anesthetics in the sample chamber 3. However, the signal does change when the energy, with which the radiation source 1 emits IR waves, decreases or fluctuates or if the window 5 or another window is contaminated. The reference receiver 6 comprises, for example, a pyroelectric detector or a plurality of thermopiles.

Contrary to prior-art photoacoustic sensors, the detection chamber 4 does not contain the gas that shall be detected, i.e., the target gas. The detection chamber 4 is rather free from a target gas. A photoacoustic sensor, in which the detection chamber 4 would contain an anesthetic, would have especially the following drawbacks:

Some anesthetics are reactive and even chemically corrosive, i.e., they react with other materials, for example, with seals or other materials of the detection chamber 4.

Some anesthetics undergo chemical changes spontaneously, especially during a more prolonged irradiation with electromagnetic waves eW.

Some anesthetics are either liquid or gaseous depending on the ambient temperature, and the state of aggregation affects the spectral absorption characteristics and may lead to a distortion of a measurement result.

Therefore, a replacement gas Eg rather than an anesthetic is present in the fluid-tight detection chamber 4. The detection chamber 4 is free from the anesthetic to be detected or from each anesthetic to be detected. The replacement gas Eg in the detection chamber 4 preferably has a partial pressure that is between 100 mbar and 2,000 mbar.

The replacement gas Eg has a spectral absorption characteristic similar to that of an anesthetic to be detected in the target gas wavelength range ZWB, i.e., here in the wavelength range from 7 µm to 10 µm.

The term "similar spectral absorption characteristic" is concretized as follows in the exemplary embodiment: The spectral overlap between the target gas, here an anesthetic, and the replacement gas Eg is above 0.2, preferably above 0.35 and especially preferably above 0.5 at least at room temperature, i.e., at an ambient temperature between 10° C. and 40° C. The spectral overlap is an indicator of the congruence between the spectral response of the transmission of the anesthetic and the spectral response of the transmission of the replacement gas Eg. The spectral overlap takes into consideration only the spectral responses in the target gas wavelength range WB and is standardized to the range of 0 to 1. The more closely the spectral responses agree in the target gas wavelength range ZWB, the greater is the spectral overlap.

The spectral response of the transmission Tr of a gas x is the function $Tr[x](\lambda)$. The spectral overlap $Ov[x,y]$ in the target gas wavelength range ZWB between two gases x and y is preferably calculated according to the formula $$Ov[x, y] = \frac{\left\{\int_{\lambda_{min}}^{\lambda_{max}} [1 - Tr[x](\lambda)] * [1 - Tr[y](\lambda)] d\lambda\right\}^2}{\left\{\int_{\lambda_{min}}^{\lambda_{max}} [1 - Tr[x](\lambda)]^2 d\lambda\right\} * \left\{\int_{\lambda_{min}}^{\lambda_{max}} [1 - Tr[y](\lambda)]^2 d\lambda\right\}}$$

The transmission and the extinction of a gas may also depend on the partial pressure of this gas in a gas mixture. The above formula, with which the spectral overlap between the gases x and y is preferably calculated, depends less strongly than other possible calculation instructions on different partial pressures in the sample chamber 3 and in the detection chamber 4.

The spectral overlap $Ov[x,y]$ is calculated in practice by a numerical integration with an increment of $[\lambda_{max}-\lambda_{min}]/N$, for which the values of the transmissions $Tr[x](\lambda i)$ and $Tr[y](\lambda i)$ are used for N+1 different wavelengths $\lambda_0, \ldots, \lambda_N$, for example, $\lambda i=\lambda_{min}+i/N*[\lambda_{max}-\lambda_{min}]$ (i=0, 1, . . . , N). These values $Tr[x](\lambda i)$ and $Tr[y](\lambda i)$ for the transmissions are known in many cases or can be determined empirically.

The spectral overlap $Ov[x,y]$ of a gas x with itself equals 1. If the gas x has a transmission of 1 in the entire target gas wavelength range ZWB and the gas y has a transmission of 0 (a theoretical situation), the spectral overlap is 0. A sufficient spectral overlap is present between the target gas and the replacement gas if the overlap is above 0.2 and preferably above 0.35 and especially preferably above 0.5 according to the formula mentioned above or another suitable formula.

It was described farther above how it is ensured in a preceding calibration phase that the same sensor 100 can detect different anesthetics, wherein a user specifies the particular anesthetic gas to be detected during the use phase by means of a switch 11.

A partially fluorinated gas is preferably used as a replacement gas e.g., with a similar absorption characteristic. The C—F groups or C—Cl groups of a replacement gas now have a similar spectral absorption characteristic for electromagnetic waves eW in the infrared range as anesthetics, at least in the target gas wavelength range ZWB. FIG. 2 and FIG. 3 show the transmission ratios $Tr(\lambda)$ of five commercially available anesthetics (top) as well as the extinctions $Ex(\lambda)$ of two partially fluorinated replacement gases (bottom), namely, the propellant R134a (tetrafluoroethane) and the propellant R227ea (heptafluoropropane). The extinction $Ex(\lambda)$ is plotted on the right-hand y axis.

The replacement gas Eg used can be handled in a simpler manner than the anesthetic or an anesthetic to be detected or each anesthetic to be detected. This means that at least one of the following properties is satisfied and all properties are ideally satisfied:

The replacement gas Eg has a lower chemical reactivity, i.e., it is chemically more inactive than the anesthetic. The replacement gas Eg is ideally chemically inert, at least in respect to each material that is used in the sensor 100.

The replacement gas Eg is gaseous in the temperature range being considered. In case of use in a closed room, this temperature range (at the usual room temperature) is preferably between 10° C. and 40° C.

The replacement gas Eg changes to a lesser extent over time than does the anesthetic, even in case of a prolonged irradiation by electromagnetic waves eW in the infrared range. The replacement gas Eg does not ideally change at all.

In a preferred embodiment, the detection chamber 4 is filled with a mixture of a gas, which has an absorption characteristic similar to that of at least one anesthetic to be detected, as well as with a diluting gas, which has a transmission above 0.9 in the entire target gas wavelength range ZWB. For example, nitrogen ($N_2$) is used as the diluting gas. Nitrogen has a transmission Tr above 0.99 in the entire target gas wavelength range ZWB, i.e., it hardly influences the generation of the acoustic effect. However, the addition of the diluting gas causes the electromagnetic waves eW to be absorbed less intensely in the detection chamber 4 and the acoustic effect is therefore stronger. The mixture of the replacement gas proper and the diluting gas acts as the replacement gas Eg, which has a spectral overlap above 0.2 in the target gas wavelength range ZWB.

While specific embodiments of the invention have been shown and described in detail to illustrate the application of the principles of the invention, it will be understood that the invention may be embodied otherwise without departing from such principles.

LIST OF REFERENCE CHARACTERS

1 Radiation source, emits IR waves
2 Housing of the photoacoustic sensor 100
3 Sample chamber, holds a sample Gp of a gas mixture to be tested 4 Fluid-tight detection chamber, contains the replacement gas Eg
5 Window in front of the detection chamber 4
6 Reference receiver, yields a correction factor
7 Acoustic receiver in the form of a microphone, measures the acoustic effect, which is generated by the electromagnetic waves eW in the detection chamber 4
8 Analysis unit, receives signals from the microphone 7 and from the reference receiver 6 and optionally from the pressure sensor 13, has read access to the memory 9
9 Memory, contains at least one respective concentration relationship between microphone signal and target gas concentration for each gas to be detected
10 Inlet in the sample chamber 3, secured by a mechanical filter
11 Switch, with which a user can select an anesthetic to be detected
12 Modulator; it modulates the electromagnetic waves eW emitted by the radiation source 1
13 Pressure sensor, which measures the pressure in the sample chamber 3
14 Optical band pass filter between the radiation source 1 and the sample chamber 3
15 Power supply unit of the sensor 100
16 Thermometer; it measures the temperature of the environment around the sensor 100
100 Photoacoustic sensor; it comprises the radiation source, the band pass filter 14, the modulator 12, the sample chamber 3, the detection chamber 4, the window 5, the reference receiver 6, the acoustic receiver 7, the thermometer 16, the analysis unit 8, the memory 9, the switch 11, the power supply unit 15 and the housing 2
Eg Replacement gas in the detection chamber 4
eW Electromagnetic waves, emitted by the radiation source 1, they pass through the sample chamber 3 and the detection chamber 4
Ex[x]=Extinction (degree of absorption) of gas x as a function of the wavelength λ, it is
Ex[x](λ) a number >=0
Gp Gas sample to be tested for anesthetic in the sample chamber 3
$\lambda_{max}$ Upper limit of the target gas wavelength range ZWB, e.g., 10μ
$\lambda_{min}$ Lower limit of the target gas wavelength range ZWB e.g., 7μ.
Tr[x]=Transmission (transmission ratio) of the gas x, percentage of the intensity after
Tr[x](λ) passage of the gas x as a function of the wavelength λ; it is a number between 0 and 1
Um Environment, which may contain an anesthetic, which shall be detected; it is in a fluid connection with the sample chamber 3
ZWB Target gas wavelength range, in which a target gas to be detected attenuates the electromagnetic waves eW, it ranges from $\lambda_{min}$ to $\lambda_{max}$

What is claimed is:

1. A photoacoustic sensor for detecting at least one target gas in an area, the sensor comprising:
   a sample chamber in a fluid connection with the area and configured to receive a gas sample from the area;
   a radiation source configured to emit electromagnetic waves in a direction of the sample chamber, wherein the wavelength range of the emitted electromagnetic waves comprises a target gas wavelength range, in which the target gas to be detected or each target gas to be detected attenuates an intensity of electromagnetic waves;
   a detection chamber being fluid-tightly sealed against an environment of the detection chamber, wherein the detection chamber is free from the target gas to be detected or free from any target gas to be detected and is filled with a replacement gas; and
   an acoustic receiver, wherein:
   the sensor is configured such that emitted electromagnetic waves pass through the sample chamber and the detection chamber and the electromagnetic waves elicit in the detection chamber an acoustic effect, which is correlated with the intensity of the electromagnetic waves passing through the detection chamber, during passage thereof through the detection chamber;
   the acoustic receiver is configured to measure an indicator of the acoustic effect elicited by the electromagnetic waves in the detection chamber and to generate a signal for the measured acoustic effect;
   at least at an ambient temperature between 10° C. and 40° C., the replacement gas is chemically more inert than the target gas to be detected or each target gas to be detected and a spectral overlap between the target gas to be detected or at least one target gas to be detected and the replacement gas is above 0.2 in the target gas wavelength range; and
   the spectral overlap between the target gas and the replacement gas is an indicator standardized to the range between 0 and 1 for a congruence between the spectral response of the transmission of the target gas and the spectral response of the transmission of the replacement gas in the target gas wavelength range.

2. The photoacoustic sensor in accordance with claim 1, wherein the replacement gas is gaseous at an ambient temperature between 10° C. and 40° C., both with electromagnetic waves passing through the detection chamber and with no electromagnetic waves passing through the detection chamber.

3. The photoacoustic sensor in accordance with claim 1, wherein the replacement gas is chemically more stable than the target gas to be detected or each target gas to be detected.

4. The photoacoustic sensor in accordance with claim 1, wherein the sensor is configured such that the target gas wavelength range comprises the range from 7 μm to 10 μm.

5. The photoacoustic sensor in accordance with claim 1, wherein the replacement gas comprises a partially fluorinated hydrocarbon.

6. The photoacoustic sensor in accordance with claim 1, wherein the replacement gas comprises a diluting gas which has a transmission above 0.9 in the target gas wavelength range.

7. The photoacoustic sensor in accordance with claim 1, further comprising a reference receiver, wherein:
   the reference receiver is configured to measure an indicator of the intensity of the electromagnetic waves passing through the detection chamber in a reference wavelength range;
   the reference wavelength range is disjunct from the target gas wavelength range; and
   the reference receiver is configured to generate a signal for the indicator of the intensity of the electromagnetic waves, in the reference wavelength range, passing through the detection chamber.

8. The photoacoustic sensor in accordance with claim 1, further comprising a memory and a data-processing analysis unit, wherein:
   a computer-evaluable concentration relationship between the concentration of the target gas in the detection chamber and the measurable indicator of the acoustic effect elicited in the detection chamber is stored in the memory for at least one target gas to be detected; and the analysis unit is configured to determine the concentration of the target gas or each target gas in the sample chamber as a function of the signal of the acoustic receiver and using of the concentration relationship.

9. The photoacoustic sensor in accordance with claim, 8, further comprising a selection unit for use by a person, wherein:

the selection unit is configured to detect a selection of a target gas to be detected;

a respective computer-evaluable concentration relationship is stored in the memory for at least two different differing target gases, which can be selected by means of the selection unit; and the analysis unit is configured to determine the concentration of the selected target gas in the sample chamber and to use for this the concentration relationship that is stored in the memory for the selected target gas.

10. A process for detecting at least one target gas in an area with the use of a photoacoustic sensor, which photoacoustic sensor comprises a radiation source, a sample chamber, a detection chamber and an acoustic receiver, wherein a target gas wavelength range, in which a target gas to be detected or each target gas to be detected attenuates an intensity of electromagnetic waves is predefined, wherein the detection chamber is fluid-tightly sealed against an area around the detection chamber and is free from the target gas to be detected or each target gas to be detected and is filled with a replacement gas, the process comprising the steps of:

bringing about a state of the sensor in which a gas sample flows from the area into the sample chamber;

with the radiation source, emitting electromagnetic waves in a direction of the sample chamber such that emitted electromagnetic waves pass through the sample chamber and the detection chamber, wherein a wavelength range of the emitted electromagnetic waves comprises the target gas wavelength range and during passage of the emitted electromagnetic waves through the detection chamber, the electromagnetic waves elicit in the detection chamber an acoustic effect, which is correlated with the intensity of the electromagnetic waves passing through the detection chamber;

with the acoustic receiver, measuring an indicator of the acoustic effect elicited in the detection chamber by the electromagnetic waves; and with the acoustic receiver generating a signal for the measured indicator of the acoustic effect, wherein:

at least at an ambient temperature between 10° C. and 40° C., the replacement gas is chemically more inactive than the target gas to be detected or each target gas to be detected and a spectral overlap between the target gas to be detected or each target gas to be detected and the replacement gas is above 0.2 in the target gas wavelength range; and the spectral overlap between the target gas and the replacement gas is an indicator standardized to a range between 0 and 1 for a congruence between the spectral response of the transmission of the target gas and the spectral response of the transmission of the replacement gas in the target gas wavelength range.

11. The process in accordance with claim 10, wherein the target gas to be detected comprises at least one anesthetic or a solvent.

12. The process in accordance with claim 10, wherein the target gas wavelength range comprises the range from 7 μm to 10 μm.

13. The process in accordance with claim 10, wherein the replacement gas is gaseous at an ambient temperature between 10° C. and 40° C., both with electromagnetic waves passing through the detection chamber and with no electromagnetic waves passing through the detection chamber.

14. The process in accordance with claim 10, wherein the replacement gas is chemically more stable than the target gas to be detected or each target gas to be detected.

15. The process in accordance with claim 10, wherein the replacement gas comprises a partially fluorinated hydrocarbon.

16. The process in accordance with claim 10, wherein the replacement gas comprises a diluting gas which has a transmission above 0.9 in the target gas wavelength range.

17. The process in accordance with claim 10, wherein the photoacoustic sensor is provided with a reference receiver, wherein:

the reference receiver is configured to measure an indicator of the intensity of the electromagnetic waves passing through the detection chamber in a reference wavelength range, the reference wavelength range is disjunct from the target gas wavelength range; and the reference receiver is configured to generate a signal for the indicator of the intensity of the electromagnetic waves passing through the detection chamber.

18. The process in accordance with claim 10, wherein the photoacoustic sensor is provided with a memory and a data-processing analysis unit, wherein:

a computer-evaluable concentration relationship between the concentration of the target gas in the detection chamber and the measurable indicator of the acoustic effect elicited in the detection chamber is stored in the memory for at least one target gas to be detected; and the analysis unit is configured to determine the concentration of the target gas or each target gas in the sample chamber as a function of the signal of the acoustic receiver and using of the concentration relationship.

19. The process in accordance with claim 18, further comprising a selection unit for use by a person, wherein the selection unit is configured to detect a selection of a target gas to be detected;

a respective computer-evaluable concentration relationship is stored in the memory for at least two different differing target gases, which can be selected by means of the selection unit; and the analysis unit is configured to determine the concentration of the selected target gas in the sample chamber and to use for this the concentration relationship that is stored in the memory for the selected target gas.

\* \* \* \* \*